United States Patent
Corl

(10) Patent No.: US 9,345,450 B2
(45) Date of Patent: May 24, 2016

(54) FOCUSED ROTATIONAL IVUS TRANSDUCER USING SINGLE CRYSTAL COMPOSITE MATERIAL

(71) Applicant: Volcano Corporation, San Diego, CA (US)

(72) Inventor: Paul Douglas Corl, Palo Alto, CA (US)

(73) Assignee: Volcano Corporation, San Diego, CA (US)

(*) Notice: Subject to any disclaimer, the term of this patent is extended or adjusted under 35 U.S.C. 154(b) by 118 days.

(21) Appl. No.: 14/135,063

(22) Filed: Dec. 19, 2013

(65) Prior Publication Data

US 2014/0180123 A1 Jun. 26, 2014

Related U.S. Application Data

(60) Provisional application No. 61/745,425, filed on Dec. 21, 2012.

(51) Int. Cl.
*A61B 8/00* (2006.01)
*A61B 8/12* (2006.01)
(Continued)

(52) U.S. Cl.
CPC ............ *A61B 8/4483* (2013.01); *A61B 8/0891* (2013.01); *A61B 8/12* (2013.01); *A61B 8/445* (2013.01); *B06B 1/067* (2013.01); *B06B 1/0622* (2013.01)

(58) Field of Classification Search
CPC .... H01L 41/22; B06B 1/0622; B06B 1/0662; B06B 1/067; B06B 1/0655; A61B 8/4483
USPC ..................... 600/462, 467; 29/594
See application file for complete search history.

(56) References Cited

U.S. PATENT DOCUMENTS 4,692,654 A * 9/1987 Umemura ............. B06B 1/0622
310/327
5,368,035 A * 11/1994 Hamm et al. ................. 600/466
(Continued)

FOREIGN PATENT DOCUMENTS

WO WO 2011-033272 A1 3/2011

OTHER PUBLICATIONS

NPL—International Search Report and Written Opinion received in Patent Cooperation Treaty Appln No. PCT/US2013/077140, dated May 26, 2014, 13 pages.
(Continued)

*Primary Examiner* — Katherine Fernandez
*Assistant Examiner* — Katherine McDonald
(74) *Attorney, Agent, or Firm* — Haynes and Boone, LLP

(57) ABSTRACT

An ultrasound transducer for use in intra-vascular ultrasound (IVUS) imaging systems including a single crystal composite (SCC) layer is provided. The transducer has a front electrode on a side of the SCC layer; and a back electrode on the opposite side of the SCC layer. The SCC layer may have a dish shape including pillars made of a single crystal piezo-electric material embedded in a polymer matrix. Also provided is an ultrasound transducer as above, with the back electrode split into two electrodes electrically decoupled from one another. A method of forming an ultrasound transducer as above is also provided. An IVUS imaging system is provided, including an ultrasound transducer rotationally disposed within an elongate member; an actuator; and a control system controlling activation of the ultrasound transducer to facilitate imaging.

16 Claims, 9 Drawing Sheets

(51) Int. Cl.
  *A61B 8/08* (2006.01)
  *B06B 1/06* (2006.01)

(56) References Cited

U.S. PATENT DOCUMENTS

| | | |
|---|---|---|
| 5,792,058 A | 8/1998 | Lee et al. |
| 6,371,915 B1 | 4/2002 | Koger et al. |
| 2004/0015084 A1 | 1/2004 | Flesch et al. |
| 2007/0100239 A1 | 5/2007 | Nair et al. |
| 2010/0076318 A1 | 3/2010 | Rehrig et al. |
| 2010/0160788 A1 | 6/2010 | Davies et al. |
| 2010/0168582 A1 | 7/2010 | Yuan et al. |
| 2010/0240998 A1 | 9/2010 | Calisti et al. |
| 2013/0303907 A1 | 11/2013 | Corl |
| 2014/0187964 A1 | 7/2014 | Corl et al. |

OTHER PUBLICATIONS

International Search Report and Written Opinion received in Patent Cooperation Treaty Application No. PCT/US2013/075725, dated Apr. 10, 2014, 11 pages.

Sun, Ping, et al., "High Frequency PMN-PT 1-3 Composite Transducer for Ultrasonic Imaging Application," Ferroelectronics, vol. 408, No. 1, 2010, 14 pages.

\* cited by examiner

FOCUSED ROTATIONAL IVUS TRANSDUCER USING SINGLE CRYSTAL COMPOSITE MATERIAL

CROSS-REFERENCE TO RELATED APPLICATIONS

The present application claims priority to and the benefit of U.S. Provisional Patent Application No. 61/745,425, filed Dec. 21, 2012, which is hereby incorporated by reference in its entirety.

TECHNICAL FIELD

The present disclosure relates generally to intravascular ultrasound (IVUS) imaging inside the living body and, in particular, to an IVUS imaging catheter that relies on a mechanically-scanned ultrasound transducer, including embodiments where the transducer includes a single crystal composite material.

BACKGROUND

Intravascular ultrasound (IVUS) imaging is widely used in interventional cardiology as a diagnostic tool for a diseased vessel, such as an artery, within the human body to determine the need for treatment, to guide the intervention, and/or to assess its effectiveness. IVUS imaging uses ultrasound echoes to create an image of the vessel of interest. The ultrasound waves pass easily through most tissues and blood, but they are partially reflected from discontinuities arising from tissue structures (such as the various layers of the vessel wall), red blood cells, and other features of interest. The IVUS imaging system, which is connected to the IVUS catheter by way of a patient interface module (PIM), processes the received ultrasound echoes to produce a cross-sectional image of the vessel where the catheter is placed.

In a typical rotational IVUS catheter, a single ultrasound transducer element is located at the tip of a flexible driveshaft that spins inside a plastic sheath inserted into the vessel of interest. The transducer element is oriented such that the ultrasound beam propagates generally perpendicular to the axis of the catheter. A fluid-filled sheath protects the vessel tissue from the spinning transducer and driveshaft while permitting ultrasound signals to freely propagate from the transducer into the tissue and back. As the driveshaft rotates (typically at 30 revolutions per second), the transducer is periodically excited with a high voltage pulse to emit a short burst of ultrasound. The same transducer then listens for the returning echoes reflected from various tissue structures, and the IVUS imaging system assembles a two dimensional display of the vessel cross-section from a sequence of these pulse/acquisition cycles occurring during a single revolution of the transducer.

In the typical rotational IVUS catheter, the ultrasound transducer is a piezoelectric ceramic element with low electrical impedance capable of directly driving an electrical cable connecting the transducer to the imaging system hardware. In this case, a single pair of electrical leads (or coaxial cable) can be used to carry the transmit pulse from the system to the transducer and to carry the received echo signals from the transducer back to the imaging system by way of a patient interface module ("PIM") where the echo signals can be assembled into an image. An important complication in this electrical interface is how to transport the electrical signal across a rotating mechanical junction. Since the catheter driveshaft and transducer are spinning (in order to scan a cross-section of the artery) and the imaging system hardware is stationary, there must be an electromechanical interface where the electrical signal traverses the rotating junction. In rotational IVUS imaging systems, this problem can be solved by a variety of different approaches, including the use of rotary transformers, slip rings, rotary capacitors, etc.

While existing IVUS catheters deliver useful diagnostic information, there is a need for enhanced image quality to provide more valuable insight into the vessel condition. For further improvement in image quality in rotational IVUS, it is desirable to use a transducer with broader bandwidth and to incorporate focusing into the transducer. A piezoelectric micro-machined ultrasound transducer (PMUT) fabricated using a polymer piezoelectric material offers greater than 100% bandwidth for optimum resolution in the radial direction, and a spherically-focused aperture for optimum azimuthal and elevation resolution. While this polymer PMUT technology offers many advantages, the electrical impedance of the PMUT is too high to efficiently drive the electrical cable connecting the transducer to the IVUS imaging system by way of the PIM. Furthermore, the transmit efficiency of polymer piezoelectric material is much lower compared to that of the traditional lead-zirconate-titanate (PZT) ceramic piezoelectric. Therefore, the signal-to-noise ratio of a PMUT will be compromised unless the deficiency in acoustic output can be compensated for by improved transmit electronics and/or other signal processing advances.

Current approaches to form a focused ultrasound beam include the use of an acoustic lens using conventional PZT transducers. For example, a rubber lens with an acoustic velocity of 1.0 mm/μsec has been used for elevation focus in phased array ultrasound systems. These approaches pose complex fabrication problems and the difficulty of removing imaging artifacts in the resulting signal.

Accordingly, there remains a need for improved devices, systems, and methods for implementing focused piezoelectric micro-machined ultrasonic transducers within an intravascular ultrasound system.

SUMMARY

According to some embodiments, an ultrasound transducer for use in intra-vascular ultrasound (IVUS) imaging systems is provided that includes a single crystal composite (SCC) layer; a front electrode on a side of the SCC layer; and a back electrode on the opposite side of the SCC layer. In some embodiments, the SCC layer includes pillars made of a single crystal piezo-electric material. The pillars are embedded in a polymer matrix in some instances. The SCC layer has a dish shape, defined by a concave surface and opposing convex surface, in some embodiments. The back electrode is split into two electrodes electrically decoupled from one another in some implementations.

A method of forming an ultrasound transducer for use in IVUS imaging systems in some embodiments includes etching a single crystal; forming a polymer layer on the etched single crystal to form a single crystal composite (SCC) having a first thickness; placing a first electrode on a first side of the SCC; forming the SCC to a second thickness; placing a second electrode on a second side of the SCC; and placing the SCC on a molded tip.

An IVUS imaging system according to some embodiments may include an ultrasound emitter and receiver rotationally disposed within an elongate member; an actuator coupled to the ultrasound emitter, the actuator moving the ultrasound emitter through at least a portion of an arc; and a control system controlling the emission of a sequence of pulses from the ultrasound emitter and receiving from the receiver ultrasound echo data associated with the pulses, the control system processing the ultrasound echo data to generate a cross-sectional image of the vessel. In some embodiments the ultrasound emitter and receiver comprises an ultrasound transducer including a single crystal composite (SCC) layer; a front electrode; and a back electrode. In some embodiments the SCC layer includes pillars made of a single crystal piezoelectric material. The pillars are embedded in a polymer matrix in some instances. The SCC layer has a dish shape, with opposing concave and convex surfaces, in some embodiments.

These and other embodiments of the present disclosure will be described in further detail below with reference to the following drawings.

BRIEF DESCRIPTION OF THE DRAWINGS

In the figures, elements having the same reference number have the same or similar functions and/or features.

DETAILED DESCRIPTION

Figure 1:
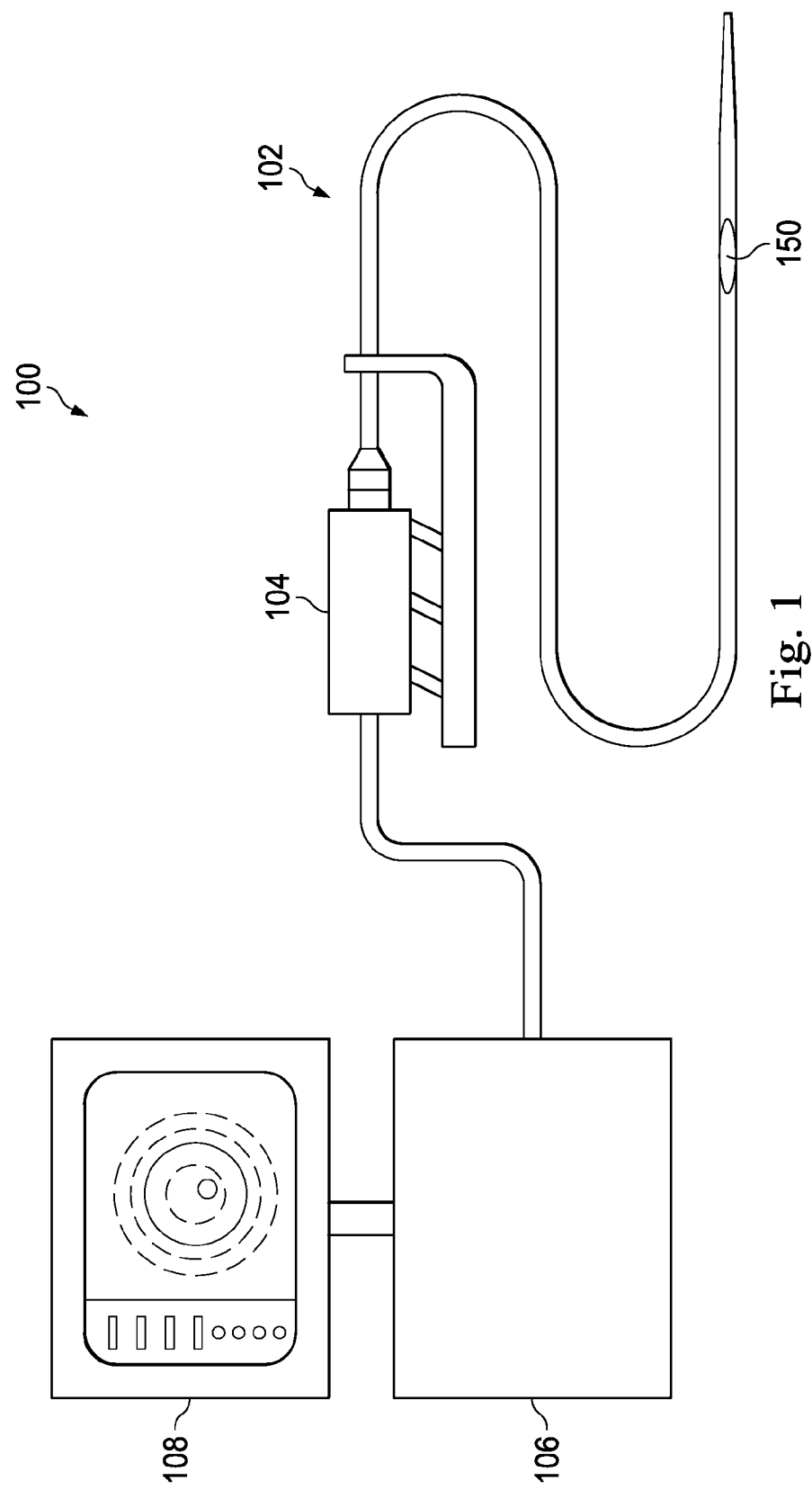
FIG. 1 is a schematic view of an imaging system according to an embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Embodiments disclosed herein are for an apparatus and a method of fabrication of the apparatus, the apparatus including a focused transducer to be used in a rotational IVUS catheter. A transducer as disclosed herein provides a broad bandwidth of ultrasound signals having focused beam propagation. Such an ultrasound beam provides a high three-dimensional (3D) resolution for ultra-sound imaging, including depth, lateral and elevation dimensions. In some embodiments, an IVUS catheter of the present disclosure provides a wide bandwidth, focused ultrasound beam without increasing the number of electrical connections to a circuit rotating together with the transducer. An ultrasound transducer according to embodiments disclosed herein may include a single crystal composite material that provides a wide bandwidth, focused beam. The single crystal composite material is shaped into an element having a curvature designed to provide a focused beam (e.g., defining a concave emitting surface for the ultrasound transducer) in some instances.

FIG. 1 shows an IVUS imaging system 100 according to an embodiment of the present disclosure. In some embodiments of the present disclosure, the IVUS imaging system 100 is a rotational IVUS imaging system. In that regard, the main components of the rotational IVUS imaging system are a rotational IVUS catheter 102, a patient interface module (PIM) 104, an IVUS console or processing system 106, and a monitor 108 to display the IVUS images generated by the IVUS console 106. Catheter 102 includes an ultrasound transducer 150 in some embodiments. PIM 104 implements the appropriate interface specifications to support catheter 102. According to some embodiments, PIM 104 generates a sequence of transmit pulse signals and control waveforms to regulate the operation of ultrasound transducer 150. PIM 104 may also receive a response signal form transducer 150 through the same pair of lines.

Ultrasound transducer 150 transmits ultrasound signals towards the vessel tissue based on the trigger signals received from PIM 104. Ultrasound transducer 150 also converts echo signals received from the vessel tissue into electrical signals that are communicated to PIM 104. PIM 104 also supplies high- and low-voltage DC power supplies to the rotational IVUS catheter 102. In some embodiments, PIM 104 delivers a DC voltage to transducer 150 across a rotational interface. Options for delivering DC power across a rotating interface include the use of slip-rings, rotary transformers, and/or the implementation of the active spinner technology.

Figure 2:
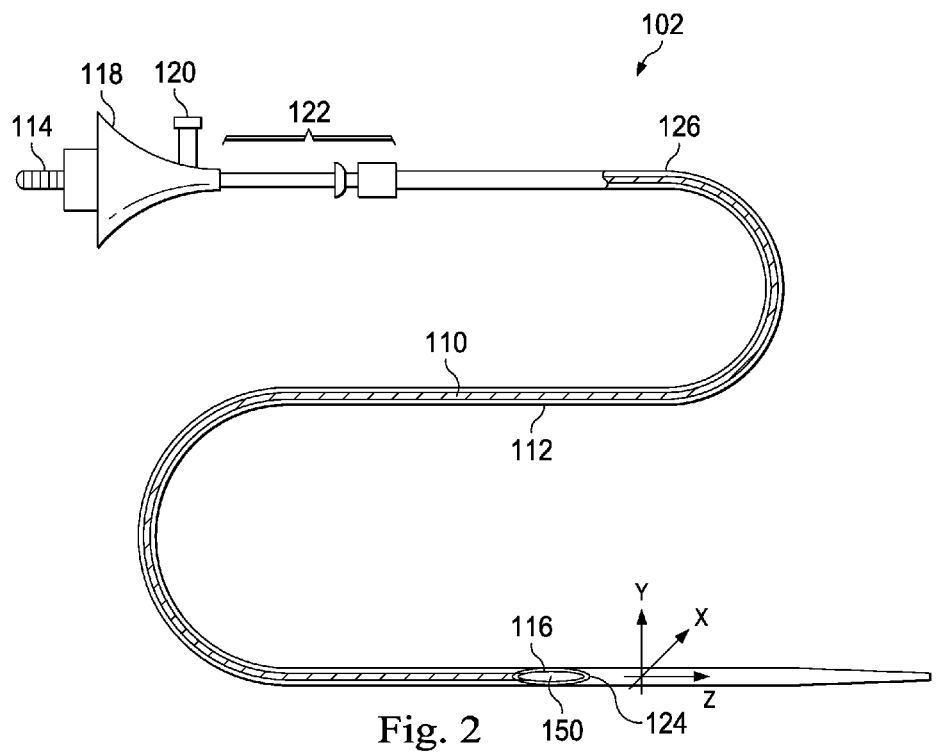
FIG. 2 is a diagrammatic, partial cutaway perspective view of an imaging device according to an embodiment of the present disclosure.

FIG. 2 shows a diagrammatic, partial cutaway perspective view of catheter 102, according to an embodiment of the present disclosure. FIG. 2 shows additional detail regarding rotational IVUS catheter 102. Rotational catheter 102 includes an imaging core 110 and an outer catheter/sheath assembly 112. Imaging core 110 includes a flexible drive shaft that is terminated at the proximal end by a rotational interface 114 providing electrical and mechanical coupling to PIM 104 (cf. FIG. 1). The distal end of the flexible drive shaft of the imaging core 110 is coupled to a transducer housing 116 containing ultrasound transducer 150 and associated circuitry.

Catheter/sheath assembly 112 includes a hub 118 supporting rotational interface 114 and provides a bearing surface and a fluid seal between rotating and non-rotating elements of catheter 102. In some embodiments, hub 118 includes a luer lock flush port 120 through which saline is injected to flush out the air and fill the inner lumen of the sheath with an ultrasound-compatible fluid at the time of use of the catheter. Saline also provides a biocompatible lubricant for the rotating driveshaft. In some implementations, hub 118 is coupled to a telescope 122 that includes nested tubular elements and a sliding fluid seal that permits catheter/sheath assembly 112 to be lengthened or shortened. Telescope 122 facilitates axial movement of the transducer housing within an acoustically transparent window 124 at the distal portion of catheter 102.

In some embodiments, window 124 is composed of thin-walled plastic tubing fabricated from material(s) that readily conduct ultrasound waves between the transducer and the vessel tissue with minimal attenuation, reflection, or refraction. A proximal shaft 126 of catheter/sheath assembly 112 bridges the segment between telescope 122 and window 124. In some embodiments, proximal shaft 126 is composed of a material or composite that provides a lubricious internal lumen and optimum stiffness to catheter 102. Embodiments of window 124 and proximal shaft 126 in catheter 102 may be as described in detail un US Pat. Application entitled "Intravascular Ultrasound Catheter for Minimizing Image Distortion," U.S. Patent Application No. 61/746,958 filed on Dec. 28, 2012, now published as U.S. Patent Application Publication No. 2014/0187964 A1 on Jul. 13, 2014, the contents of which are hereby incorporated in their entirety by reference, for all purposes.

Figure 3:
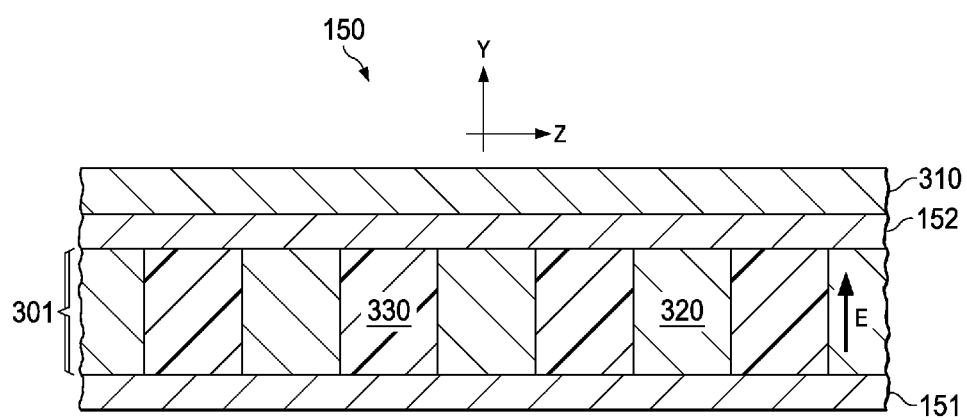
FIG. 3 shows a partial view of an ultrasound transducer according to an embodiment of the present disclosure.

FIG. 3 shows a partial view of ultrasound transducer 150 according to some embodiments disclosed herein. Transducer 150 includes a single crystal composite material (SCC) 301 having pillars 320 of a single crystal piezo-electric material embedded in a polymer matrix 330. In some embodiments polymer matrix 330 is formed by epoxy. The epoxy used as filler in polymer matrix 330 provides flexibility to the SCC material forming ultrasound transducer 150.

In some embodiments, an impedance matching layer 310 is included in ultrasound transducer 150. Impedance matching layer 310 facilitates coupling of the acoustic wave with the medium surrounding ultrasound transducer 150. Soft polymer matrix 330 reduces the acoustic impedance to SCC 301, thus providing high efficiency and broad bandwidth to transducer 150 for acoustic coupling. In some embodiments, matching layer 310 may be a quarter-wave matching layer added to SCC 301, to further improve efficiency and bandwidth of transducer 150, thus enhancing sensitivity.

According to some embodiments disclosed herein, pillars 320 form structures elongated in an axial direction (Y-axis in FIG. 3) having a narrow diameter in cross section (Z-axis in FIG. 3). The cross section of pillars 320 is in a plane of SCC 301 forming ultrasound transducer 150. Further according to some embodiments, polymer matrix 330 is continuous in the axial direction (Y-axis) and in the plane of SCC 301 forming ultrasound transducer 150 (XZ-plane). The anisotropic nature of SCC 301 confines the electric field E within pillars 320, which have a high dielectric constant. Fringe fields at the edges of electrodes 151 and 152 are mitigated by polymer matrix 330. Thus, in some embodiments the performance of transducer 150 is not degraded by fringe fields at electrode boundaries. According to some embodiments, the thickness (or height) of pillars 320 may be 50 µm or less, for 40 MHz center frequency operation. In some embodiments a thickness-to-width aspect ratio of at least 2 or greater may be desirable, resulting in pillars 320 having a diameter of 20 µm or less.

Accordingly, SCC 301 can be made using deep reactive ion etching (DRIE) applied to a single crystal material. Etch a matrix pattern using DRIA and fill the etched trenches with epoxy. Then grind away back side and polish front side and have a resulting composite layer. A horizontal resonant frequency (oscillations in the XZ plane in FIG. 3) is so far apart from vertical frequency (oscillations along the Y-axis in FIG. 3) there is little energy expended by horizontal resonance. This makes the transducer more efficient. Wide bandwidth is achieved by efficiently coupling into medium (for example, using a matching layer). A matching layer overcomes acoustic impedance mismatch between transducer material and the transmitting medium. A PZT has impedance of about 30 while that of blood/saline solutions is about 1.6/1.5. A matching layer allows the transition from the PZT material to the transmitting medium more efficient. In some embodiments, the epoxy used to form SCC 301 may be used as an impedance matching layer. The impedance of epoxy is about 3, while impedance of SCC 301 depends on distribution of PZT ceramic pillars within the epoxy matrix. In some embodiments the acoustic impedance of SCC 301 may be approximately 10. Adding a matching layer and/or a backing material to transducer 150 increases the bandwidth. The shape of pillars 320 may lightly impact the device bandwidth and center frequency of operation. Acoustic loss of the epoxy matrix affects the bandwidth of transducer 150. The epoxy serves to absorb or dissipate sound. Any energy that attempts to stay in the plastic will be absorbed quickly. An added advantage of SCC 301 is the higher electric field density in pillars 320 relative to epoxy matrix 330 due to the higher dielectric constant of the PZT ceramic relative to the epoxy. This increases the coupling efficiency of the transducer.

A piezoelectric material typically has a 20:1 acoustic impedance mismatch with blood and saline. A composite material increases the proportion of epoxy and polymers in transducer 150, reducing acoustic impedance and providing better impedance matching. Bandwidth may be improved by including a backing material overlaid on transducer 150 to absorb acoustic energy, increasing bandwidth at the cost of somewhat reduced signal strength.

SCC 301 provides high efficiency and broad bandwidth for ultrasound generation and sensing, which is desirable in medical applications. According to some embodiments, single crystal piezoelectric materials used in SCC 301 have a high electromechanical coupling coefficient. The electromechanical coupling coefficient of single crystal piezoelectric materials is typically higher than PZT ceramic. Thus, the voltage levels needed for a predetermined volume change is lower for the single crystal materials used in SCC 301, relative to that of piezo-electric ceramics. This increases the power conversion efficiency of SCC 301 from radiofrequency energy into sound, and from sound into radiofrequency energy. Some embodiments include narrow pillars 320 that remove the lateral constraint on the piezoelectric material that is present in a continuous slab of material. The lateral constraint of a bulk crystal is related to the rigidity of the material, as the pillars embedded in epoxy stretch longitudinally, there is less resistance from the surrounding epoxy material since the epoxy material is less rigid. In such embodiments, low frequency lateral modes (in the XZ-plane in FIG. 3) in the vicinity of the desired ultrasound frequency are suppressed in narrow pillars 320 by the surrounding polymer matrix 330. Thus, most of the RF electrical energy in SCC 301 is transferred to 'height' vibration modes (Y-axis in FIG. 3) in pillars 320, which couple to the ultrasound waves forming the probe beam. In some embodiments, polymer matrix 330 reduces the acoustic impedance of SCC 301 compared to that of a single crystal material. Indeed, the young modulus of polymer matrix 330 is lower than that of the single crystal 320, or that of a piezo-electric ceramic. For example, in some embodiments SCC 301 may include 75% in volume of polymer matrix 330. Such a composite has low acoustic impedance compared to a slab of single crystal piezoelectric or piezo-ceramic material. This low acoustic impedance is better matched to tissue acoustic impedance, therefore providing high efficiency and broad bandwidth to SCC 301.

The dimensions of SCC 301 vary according to the specific application sought. For example, the target ultrasound frequency and bandwidth determine the specific dimensions of SCC 301 in some instances. In some embodiments pillars 320 are about 10 μm in diameter (Z-axis in FIG. 3) with 10 μm deep kerfs (pillar height, Y-axis in FIG. 3). For high frequency IVUS, it may be desirable to have even smaller structures and kerfs in SCC 301. In some embodiments single crystal materials may be desirable in SCC 301 for high frequency applications because single crystals may be patterned using deep reactive ion etching (DRIE). DRIE techniques may be used to pattern the crystalline substrate with micron accuracy to fabricate SCC 301 materials on a wafer scale.

The volume fraction of polymer matrix 330 in SCC 301 may also vary according to the specific application. For example, the volume fraction of polymer matrix 330 determines the impedance of the transducer material which is beneficial to match acoustical impedance of the tissue of interest for the use of the ultrasound beam in some instances. The thickness of the composite crystal is determined by the resonance frequency desired. The thickness of SCC 301 is chosen to obtain a pre-selected center frequency of a transmitted ultrasound signal from transducer 150.

Figure 4:
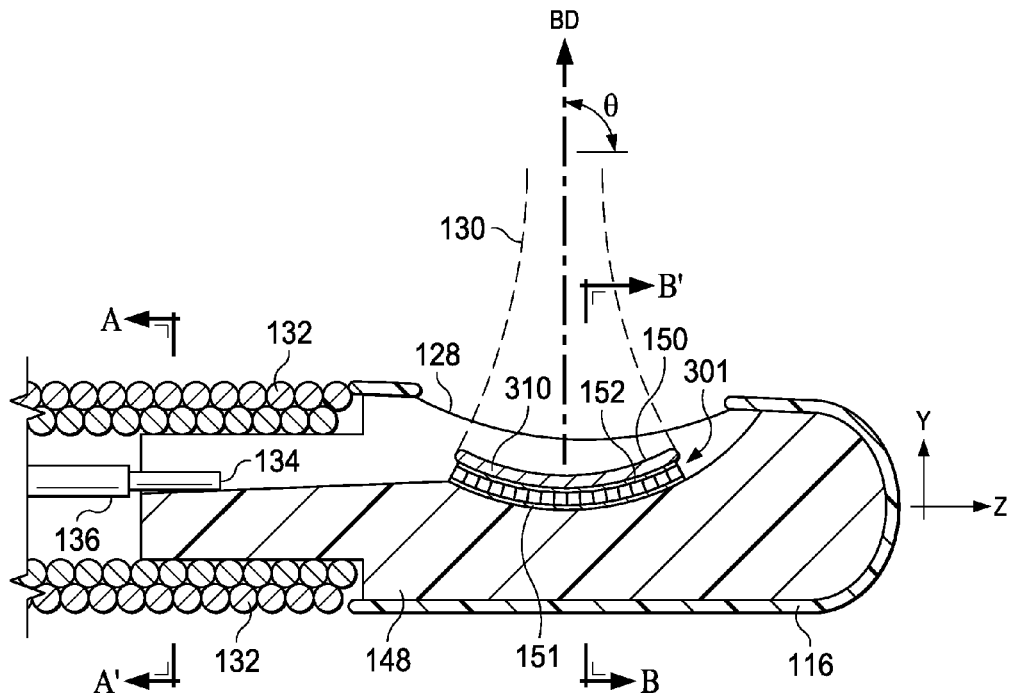
FIG. 4 shows a partial cross-sectional side view of a distal portion of an imaging device according embodiment of the present disclosure.

FIG. 4 shows a partial perspective view of transducer housing 116, including ultrasound transducer 150 according to some embodiments. Ultrasound transducer 150 includes SCC 301 and impedance matching layer 310. Other details of ultrasound transducer 150 are omitted in FIG. 4, for clarity. It is understood that ultrasound transducer 150 in FIG. 4 may include the same or similar elements as shown in FIG. 3. For example, ultrasound transducer 150 in FIG. 4 may include back electrode 151, and front electrode 152.

In some embodiments SCC 301 is deformed into a curved shape. For example, SCC 301 is deformed into a dish-shaped structure having a symmetry axis included in a plane that also includes the Z-axis in FIG. 3. In some embodiments, the dish-shaped structure may be symmetric about the BD axis, which may be parallel to the Y-axis, or may be forming an angle relative to the Y-axis. This may be desirable for providing a focused ultrasound beam. For example, in some instances SCC 301 is deformed such that the upper surface of SCC 301 as viewed in FIG. 3 becomes concave. In some implementations, the concave shape of the upper surface of SCC 301 is generally spherical. Further, in some instances the deformation of SCC 301 results in the lower surface of SCC 301 being convex. In some implementations, the convex shape of the lower surface of SCC 301 is generally spherical. In some particular implementations, the concave upper surface and the convex lower surface are both generally spherical with a common center point.

Transducer housing 116 is in a distal portion of catheter 102 according to an embodiment of the present disclosure. In particular, FIG. 4 shows an expanded view of aspects of the distal portion of imaging core 110. In this exemplary embodiment, imaging core 110 is terminated at its distal tip by housing 116. Housing 116 may be fabricated from stainless steel or other suitable biocompatible material, and have a bullet-shaped or rounded nose, and an aperture 128 for an ultrasound beam. Thus, ultrasound beam 130 may emerge from housing 116, through aperture 128. In some embodiments, flexible driveshaft 132 of imaging core 110 is composed of two or more layers of counter wound stainless steel wires. Flexible driveshaft 132 is welded or otherwise secured to housing 116 such that rotation of flexible driveshaft 132 also imparts rotation to housing 116. In the illustrated embodiment, an electrical cable 134 delivers the high-voltage transmit pulse and carries the low amplitude echo signal back to PIM 104. with an optional shield 136 provides electrical power to SCC 301. Electrical cable 134 extends through an inner lumen of flexible driveshaft 132 to the proximal end of imaging core 110 where it is terminated to the electrical connector portion of the rotational interface 114 (cf. FIG. 2). SCC 301 is mounted onto molded tip 148. Molded tip 148 may be formed of a polymer material such as epoxy, and serve as an acoustic backing material to absorb acoustic reverberations propagating within housing 116. Molded tip 148 provides strain relief for electrical cable 134 at the point of soldering to electrodes 151 and 152 in some instances. In some embodiments, a flexible sheet of material is molded into bowl shaped substrate to have a concave shape.

According to some embodiments, molded tip 148 is formed such that an upper surface of the molded tip is concave so that when ultrasound transducer 150 is placed on the concave upper surface, the flexibility of SCC 301 allows ultrasound transducer 150 to acquire a corresponding curved shape. In some instances, a bottom surface of the ultrasound transducer 150 matches the curvature of the upper surface of the molded tip 148. Accordingly, in some such instances the bottom surface of the ultrasound transducer 150 becomes convex and an opposing upper surface of the ultrasound transducer becomes concave (as shown in FIGS. 4 and 5B). The convex shape of the lower surface of the ultrasound transducer 150 may have an apex along the axis of beam direction BD such that a tangent to apex of the surface forms an angle θ with a longitudinal axis of catheter 102 (Z-direction in FIG. 4). In that regard, in some embodiments the concave upper surface of the ultrasound transducer 150 is symmetrical about the axis of beam direction BD such that ultrasound beam 130 emitted from the ultrasound transducer 150 propagates along direction BD into the vessel tissue. FIG. 4 shows a BD substantially orthogonal to the longitudinal axis of catheter 102 (0~90°). One of ordinary skill will recognize that angle θ may have values smaller than 90° or larger than 90°, depending on the desired features for ultrasound data processing. In that regard, in some implementations, the ultrasound transducer 150 is mounted such that the ultrasound beam 130 propagates at an oblique angle with respect to the longitudinal axis of the catheter.

The curvature adopted by ultrasound transducer 150 according to embodiments as disclosed herein provides focusing for beam 130. In some embodiments aperture 128 may be about 500 μm in diameter (d), and a focal length, f:3d, may be desired to obtain sufficient resolution and depth of field. Thus, the geometric focus of ultrasound beam 130 may be about 1 mm outside the sheath (1.5 mm from the aperture). For a curved transducer of this geometry, the depth of the dish should be approximately 20 μm. In some embodiments, the wavelength of a center frequency of an ultrasound signal transmitted by transducer 150 is about 40 μm in the transducer material. Accordingly, the diameter of the transducer may fit about a ten, a dozen, or a similar number of wavelengths within its surface.

In some embodiments an acoustic lens may be used to provide focusing to beam 130. To achieve a lens, some embodiments may use silicone or some other polymer that reduces sound speed through the lens material relative to that of the medium. For example, ultrasound waves may travel at a 1.0 mm/μsec velocity in a silicone lens, versus 1.5 mm/μsec medium velocity. This may provide a similar focusing power (f:3d) to the 20 μm deep dish described above with a lens thickness of approximately 60 μm. Such a lens may be formed by surface tension under a microscope, to control thickness. For example a lens may be formed with a glue drop having a concavity provided by surface tension. A material may be as silicon rubber (slow material). But careful with losses.

The curved transducer approach as shown in FIG. 4 facilitates mitigating reflections, reverberation, attenuation, and other diffraction effects resulting from using refractive elements in the path of ultrasound beam 130 in some embodiments.

Figure 5A:
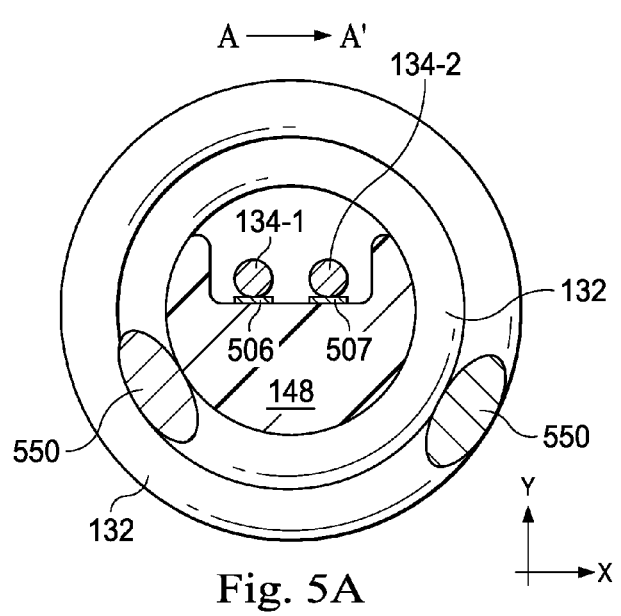
FIG. 5A shows a partial cross-sectional axial view of the distal portion of the imaging device of FIG. 4 along section line A-A'.
Figure 5B:
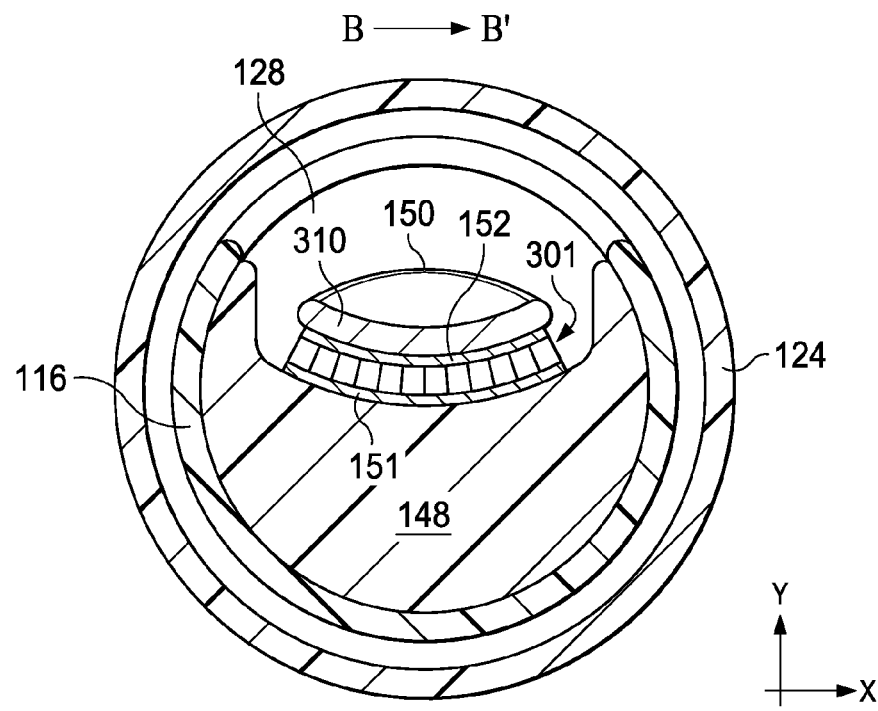
FIG. 5B shows a partial cross-sectional axial view of the distal portion of the imaging device of FIG. 4 along section line B-B'.

FIG. 5A shows a partial cross-section view of a transducer housing including electrical leads 134-1 and 134-2, according to some embodiments. FIG. 5A results from taking a cut away view of FIG. 4 along line AA'. Electrical leads 134-1 and 134-2 may be collectively referred to as leads 134 (cf. FIG. 4). Leads 134 may be coupled to bonding pad 506 (lead 134-1) and to bonding pad 507 (lead 134-2). Bonding pads 506 and 507 may have electrical contact with either of electrodes 151 and 152 in ultrasound transducer 150. In some instances, electric leads 134-1 and 134-2 provide a high and a low voltage signal coupled to SCC 301 through electrodes 151 and 152. In some embodiments lead 134-1 is coupled to back electrode 151 and lead 134-2 is coupled to front electrode 152. Further, according to some embodiments leads 134-1 and 134-2 are coupled to different portions of back electrode 151. In such configurations, front electrode 152 may have a floating voltage having a value between the voltages provided by leads 134-1 and 134-2. Embodiments having a floating electrode 152 may reduce the connections used inside housing 116. In particular, embodiments having a floating electrode 152 may enable the use of a continuous index matching layer 310.

FIG. 5B shows a partial cross-section view of transducer housing 116, including ultrasound transducer 150, according to some embodiments. FIG. 5B results from taking a cut away view of FIG. 4 along line BB'. FIG. 5B illustrates aperture 128 formed above ultrasound transducer 150 to allow ultrasound beam 130 to pass through, into and from the vessel tissue. FIG. 5B also shows window 124, which is transparent to the ultrasound beam 130 coupling transducer 150 with the vessel tissue (cf. FIG. 2).

Figure 6A:
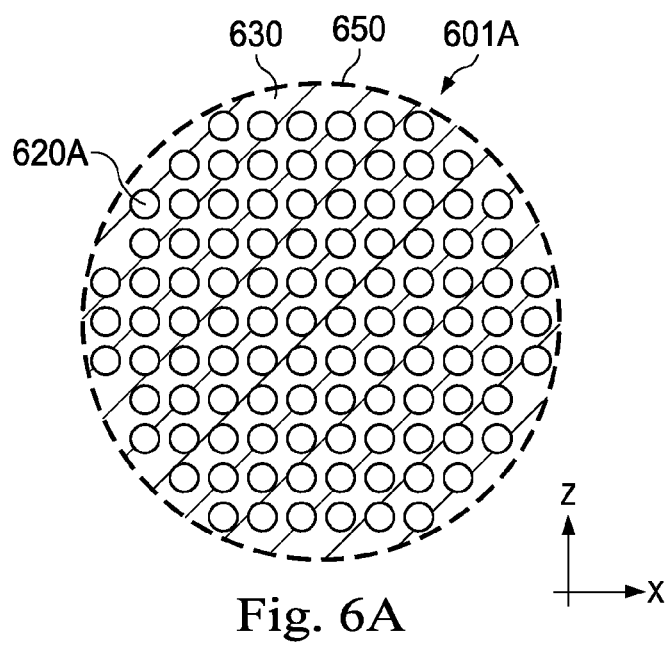
FIG. 6A shows a partial plan view of a single crystal composite according to an embodiment of the present disclosure.
Figure 6B:
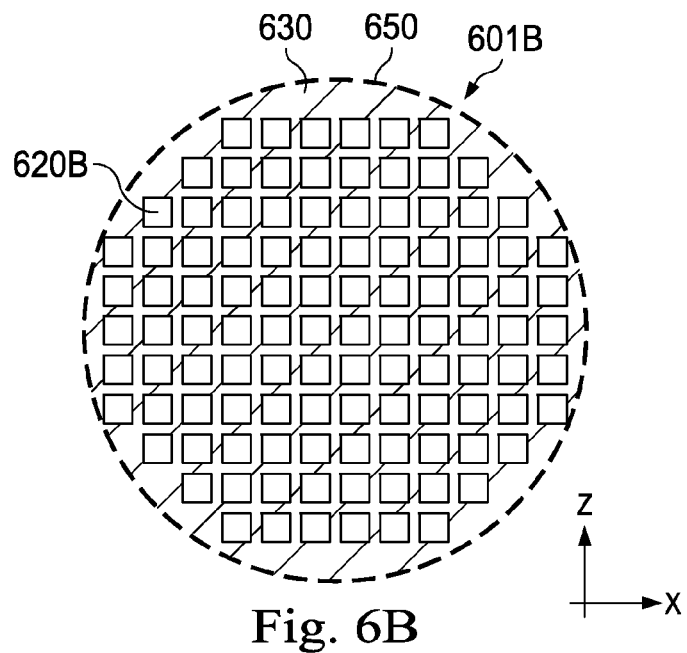
FIG. 6B shows a partial plan view of a single crystal composite according to another embodiment of the present disclosure.
Figure 6C:
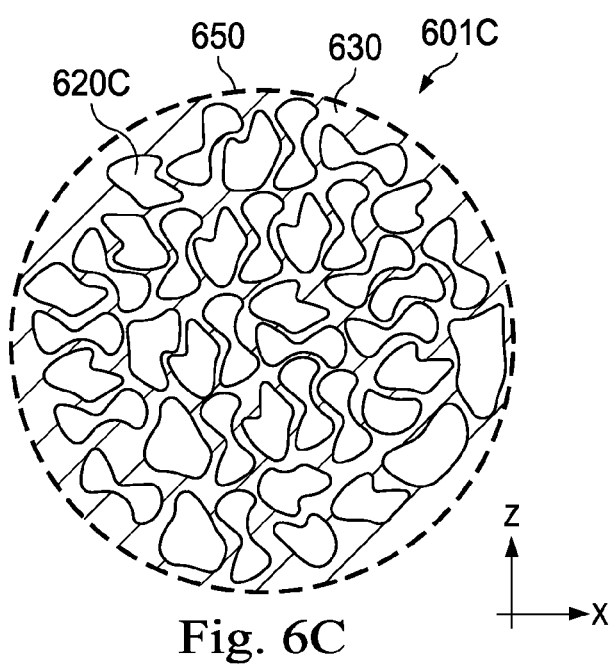
FIG. 6C shows a partial plan view of a single crystal composite according to yet another embodiment of the present disclosure.

FIGS. 6A, 6B, and 6C show partial plan views of single crystal composites 601A, 601B, and 601C, respectively, according to embodiments disclosed herein. Without loss of generality, SCC 601A, SCC 601B, and SCC 601C in FIGS. 6A, 6B, and 6C are shown in a plane XZ consistent with Cartesian coordinate axes shown in FIGS. 1-5B. One of ordinary skill in the art will recognize that an ultrasound transducer fabricated from any one of SCC 601A, 601B, and 601C may have any orientation in 3D space. In particular, as has been discussed above, an ultrasound transducer formed from SCC 601A, SCC 601B, and SCC 601C may have a 3D curvature forming a dish shape having a symmetry axis, BD, as shown in FIG. 4. SCC 601A, SCC 601B, and SCC 601C (collectively referred to as SCC 601) include pillars 620A, 620B, and 620C, respectively (collectively referred to as pillars 620). Pillars 620 in SCC 601 are embedded in polymer matrix 630. In some embodiments polymer matrix 630 may be as polymer matrix 330, described in detail with reference to FIG. 3, above. Also illustrated in FIGS. 6A, 6B, and 6C is a cutout path 650 in the XZ plane. Cutout path 650 may be formed with a laser beam on portions of SCC 601 including polymer matrix 630.

One of ordinary skill will recognize that the portion of the total area of SCC 601A, 601B, and 601C covered by pillars 620A, 620B, and 620C may vary. In some embodiments pillars 620A, 620B, and 620C may cover an area of about 25% of a surface area of SCC layer 601A, 601B, and 601C, respectively.

As shown in FIG. 6A, SCC 601A includes pillars 620A having a circular cross-section in the XZ plane. As shown in FIG. 6B, SCC 601B includes pillars 620B having a square cross-section in the XZ plane. As shown in FIG. 6C, SCC 601C includes pillars 620C having puzzle-piece cross-section in the XZ plane. One of ordinary skill would recognize that the particular shape of pillars in SCC 601 in the XZ plane is not limiting. Some embodiments may include pillars having cross-sections in the XZ plane with dog-bone shape, pseudo-random shape, and hexagonal shape.

Embodiments such as SCC 601A, 601B, 601C, or similar non-traditional shapes provide improved fill efficiency in the XZ plane, improved adhesion to polymer matrix 630, greater flexibility, and better suppression of undesired lateral modes (in the XZ plane). Furthermore, SCC 601 provides improved mechanical integrity during the wafer thinning process. Patterning the finished transducer with cutout path 650 is also a valuable benefit. In some embodiments, cutout path 650 may form a circular or elliptical transducer shape. Ultrasound transducers having circular or elliptical shapes offer good performance in terms of side-lobe levels, compared to cutout paths having rectangular or square shapes.

The geometrical configuration of pillars 620 shown in FIG. 6 is not limiting to patterns 620A, 620B, or 620C. One of ordinary skill will recognize that many configurations are possible. In some embodiments the aperture formed by SCC 601 may be apodized by adjusting the density of pillars 620 near the edges of the aperture (close to cutout path 650) to further reduce side-lobe levels. Some embodiments include pillars 620 having cross-sections with shapes obtained from Escher style tessellations of XZ-plane. In some embodiments, odd-shaped but uniform pillars 620 are used.

Figure 7A:
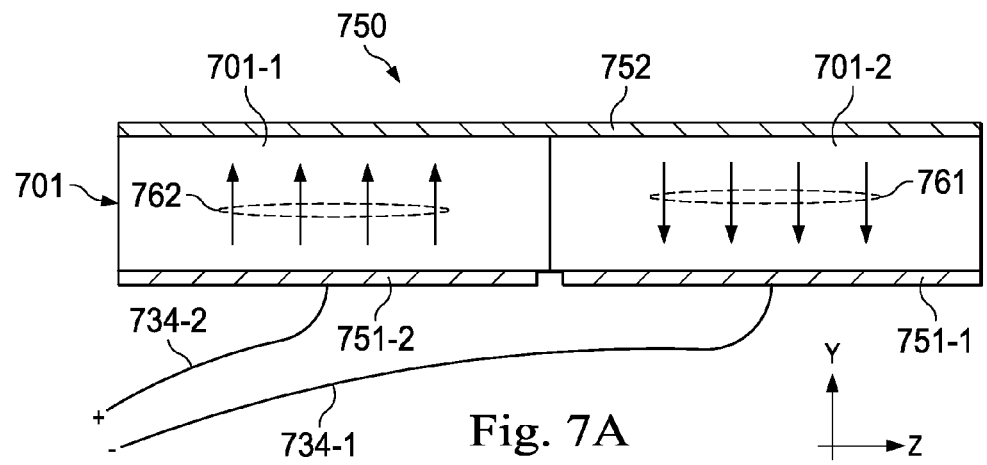
FIG. 7A shows a partial side view of an ultrasound transducer according to an embodiment of the present disclosure.

FIG. 7A shows a partial side view of an ultrasound transducer 750 according to some embodiments disclosed herein. Embodiments of split back electrode transducer 750 include a back electrode divided into two equal halves 751-1 and 751-2. In some embodiments, halves 751-1 and 751-2 have a D-shape where the transducer has a circular or elliptical profile. Halves 751-1 and 751-2 are electrically decoupled from one another, so that each half may be coupled to a different voltage. The front electrode is continuous over the entire front surface of transducer 750 in some instances. In ultrasound transducer 750 the electrode connections to electrical cables 734-1 and 734-2 are provided from the back side. Thus, the back electrode in ultrasound transducer 750 includes back side portion 751-1 connected to cable 734-1, and back side portion 751-2 connected to cable 734-2. According to some embodiments, front electrode 752 may float with no direct contact to an outside voltage source, or ground. Ultrasound transducer 750 includes SCC 701, which may include single crystal pillars embedded in a polymer similar to SCC 301 and SCC 601 as described in detail above (cf. FIGS. 1, 6A, 6B, and 6C).

Some embodiments of ultrasound transducer 750 with a split back electrode configuration as in FIG. 7A include SCC 701 having two halves 701-1 and 701-2, poled in opposite directions. For example, a first half SCC 701-1 coupled to electrode 751-1 may be poled in a first direction, and a second half SCC 701-2 coupled to electrode 751-2 may be poled in a second direction opposite to the first direction. SCC may support a split polarization without significant artifacts due to the separation between individual pillars provided by the polymer matrix. According to some embodiments, cable 734-1 may couple electrode 751-1 to a voltage supply at a first voltage. Also, cable 734-2 may couple electrode 751-2 to a voltage supply at a second voltage, higher than the first voltage. When the two back electrodes are excited with equal and opposite signals, the front electrode remains at virtual ground by symmetry, and each of transducer halves 701-1 and 701-2 receive equal and opposite electrical excitation. Electric field 761 is opposite in direction to electric field 762. Likewise, the polarization induced in SCC 701-1 by electric field 761 is opposite to the polarization induced in SCC 701-2 by electric field 762. Since SCC 701-1 and SCC 701-2 are poled in opposite directions, the piezo-electric effect on first half 701-1 is the same as the piezo-electric effect on second half 701-2. Thus, an acoustic wave-front including the two halves of split electrode transducer 750 is generated. Accordingly, in some embodiments halves 701-1 and 701-2 vibrate in phase with one another, providing a full aperture beam.

A single crystal composite as disclosed herein is particularly well suited to the split back electrode configuration. Fringe fields at the boundary between the split electrodes 751-1 and 751-2 are mitigated by polymer matrix 330. This ensures that poling of halves 701-1 and 701-2 provides a well-defined orientation near their border.

Some embodiments using ultrasound transducer 750 including a split electrode may yield a lower capacitance (higher impedance) device. Indeed, each of the two capacitors formed between electrode 751-1, 752, and 751-2 has a lower capacitance than a capacitor made of the same SCC 701 material and having the same thickness, but double the area. Furthermore, in the split electrode configuration the two capacitors formed between electrodes 751-1, 752, and 751-2 are connected in series, thus reducing the net capacitance of SCC 701 as compared to a configuration where back electrodes 751-1 and 751-2 form a single electrode. Thus, embodiments of SCC 701 having a split back electrode may use a higher excitation voltage to achieve the same ultrasound output as a conventional electrode. Embodiments consistent with the split electrode configuration illustrated in FIG. 7A provide desirable manufacture features, since front electrode 752 is floating and may not use a direct connection to a voltage source, or ground. This simplifies the configuration and manufacturing of ultrasound transducer 750 and tip housing 116. For example, an impedance matching layer such as layer 310 (cf. FIG. 3) may be formed as a continuous layer on top of front electrode 752.

Split back electrode transducer 750 is desirable in embodiments including matching layer 310. The use of a split back electrode permits matching layer 310 to be formed at the wafer level fabrication of transducer 750 without having a conductive material making contact with front electrode 752. Thus, fabrication methods according to some embodiments may avoid cutting a hole in matching layer 310 for a front electrode contact.

Figure 7B:
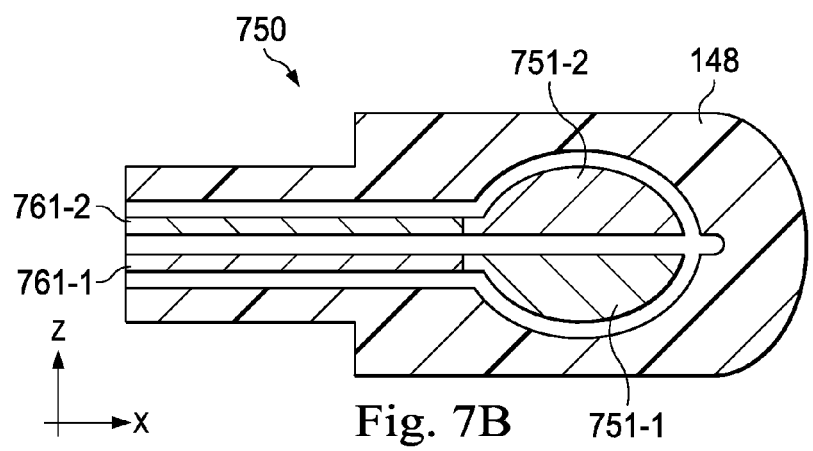
FIG. 7B shows a partial plan view of a distal portion of an imaging device incorporating the ultrasound transducer of FIG. 7A according to an embodiment of the present disclosure.

FIG. 7B shows a partial plan view of ultrasound transducer 750 according to some embodiments disclosed herein. FIG. 7B illustrates back electrodes 751-1 and 751-2. FIG. 7B also illustrates molded tip 148 (cf. FIG. 4). In some embodiments electrodes 751-1 and 751-2 in the distal area close to the tip of molded tip 748 may include a gold plated diamond grit. Bond pads 761-1 and 761-2 provide electrical contact to electrodes 751-1 and 751-2 from electrical cables such as cables 134-1 and 134-2 (cf. FIG. 5A). Such configuration ensures efficient and reliable electrical contact to SCC 701. Bond pads 761-1 and 761-2 may be formed of any conductive material, like gold or silver. One of ordinary skill would recognize that the specific material forming bond pads 761-1 and 761-2 is not limiting and any conductive material or alloy thereof may be used, without limitation.

In embodiments using a gold plated diamond grit, SCC 701 is pressed and glued onto molded tip 148. Thus, protuberances in the diamond grit poke into the electrode plating on the back of the sheet formed by SCC 701, providing a low resistance electrical connection. Some embodiments may include anisotropic conductive adhesives to provide a reliable electrical connection to SCC 701. For example, an insulating epoxy-like material filled with gold or silver spheres provides an anisotropic conductive adhesive in some implementations. In such embodiments the density of the conductive spheres is low enough that the material is non-conductive, but when the material is compressed into a thin film between two conductive surfaces, the spheres are squished between the conductors and they bridge the narrow gap to again form a low resistance connection along the compression direction.

Figure 7C:
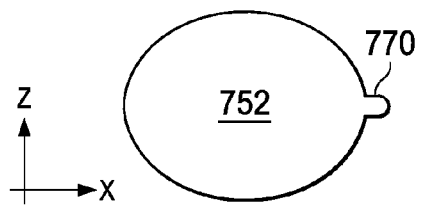
FIG. 7C shows a partial plan view of the ultrasound transducer of FIG. 7A according to an embodiment of the present disclosure.

FIG. 7C illustrates front electrode 752, which may be the common electrode for SCC transducer 750. In some embodiments electrode 752 includes alignment tab 770 to orient the device properly within molded tip 148. The SCC may include an epoxy matching layer. An acoustic impedance approximately equal to 3 is desirable.

According to some embodiments, SCC 701 including electrodes 752, 751-1, and 751-2 is glued into molded tip 148 forming a dish-shape for providing focused beam 130 (cf. FIG. 4).

Figure 8A:
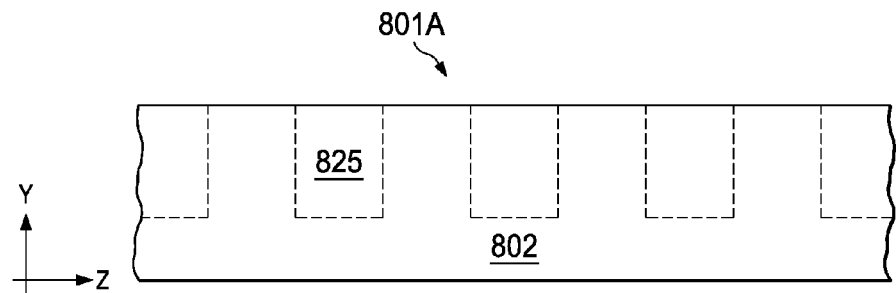
FIGS. 8A-F show a series of partial cross-sectional side views of fabrication stages for an ultrasound transducer according to some embodiments of the present disclosure.
Figure 8B:
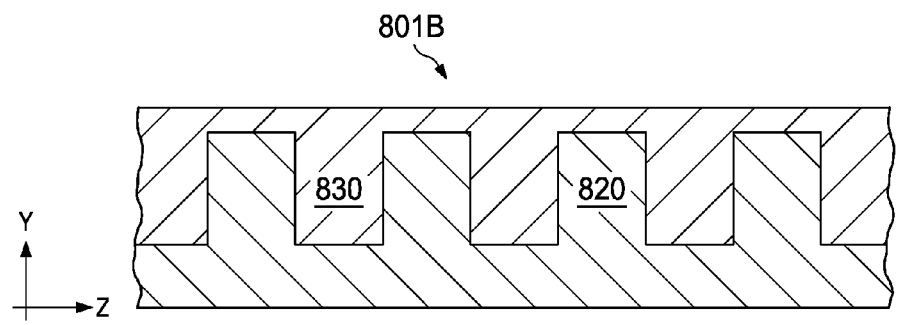

FIGS. 8A-F show a partial view of fabrication stages for an SCC 801, according to some embodiments. FIG. 8A illustrates single crystal material 802 formed into a slab of material 801A, patterned using photolithography and DRIE (or other suitable etching and/or material removal processes) to etch away portions 825 of material. SCC material 802 may be any single crystal, piezo-electric material. For example, some embodiments may use a single crystal including lead magnesium niobate-lead titanate (PMN-PT). Slab 801A may be formed on a wafer, having a front surface (top of FIG. 8A) and a back surface (bottom of FIG. 8B). This leads to a slab of material 801B having isolated pillars or ribs 820, partially formed through the wafer, as illustrated in FIG. 8B. In some embodiments a pattern of trenches is etched in the piezo-electric substrate using DRIE to produce vertical walls (Y-direction) and a very precise geometry (XZ plane), typically with 1 μm resolution. After etching, the trenches are filled with a polymer 830 such as epoxy or silicone, as illustrated in FIG. 8B.

Figure 8C:
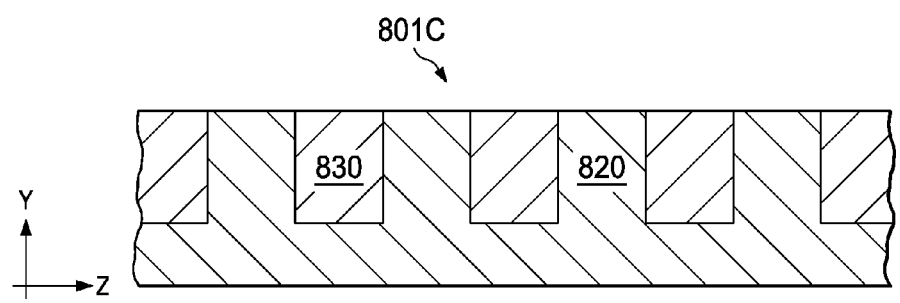

FIG. 8C illustrates the forming of slab 801C, according to some embodiments. Polymer layer 830 may be on the front side of the ultrasound transducer in slab 801B, and material 802 may be on the back side of slab 801B. In some embodiments polymer layer 830 may be polished, ground, or etched to a thickness such that polymer layer 830 and pillars 830 have an edge on the front side of SCC 801.

Thus, slab 801C includes pillars 820 of a piezo material, isolated from one another on the front side (top of FIG. 8C), contained within polymer matrix 830. The flexibility of slab 801C is adjustable based on the size of the trenches formed in the DRIE step and the properties of the polymer used in matrix 830. Further, slabs 801C may have different geometries obtained by photolithography and DRIE steps, as described above. In some embodiments, the pattern of pillars 820 may be isolated islands separated by large moats.

Figure 8D:
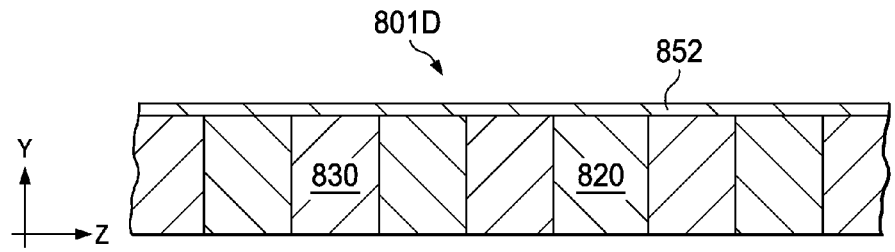

FIG. 8D illustrates forming of slab 801D, including a front electrode 852. Forming slab 801D may include forming the SCC layer into a desired thickness. To accomplish this, material 802 in the back side of slab 801C (bottom of FIG. 8C) may be polished, ground, or etched to a thickness such that polymer matrix 830 and pillars 820 have an edge on the back side of SCC 801D. When the substrate is thinned to form a composite sheet having pillars 820 embedded in polymer matrix 830, individual transducer elements forming an aperture can be selected by tracing a desired outline and removing polymer matrix 830. In some embodiments, tracing the desired outline of individual elements and removing the polymer may be performed using a laser. The individual transducer elements are then electroplated to form a front electrode 852 in slab 801D in some instances. Front electrode 852 is formed by electroplating a conductive material on the top portion of slab 801D in some implementations. In some embodiments front electrode 852 and matching layer 810 are formed while the structure is part of the single wafer. The thickness of the structure may be 50 µm, 40 µm, 30 µm, or less. In some embodiments, the epoxy layer may be ground to form an impedance matching layer having a ¼ wavelength thickness (or approximately 15 µm in epoxy).

Figure 8E:
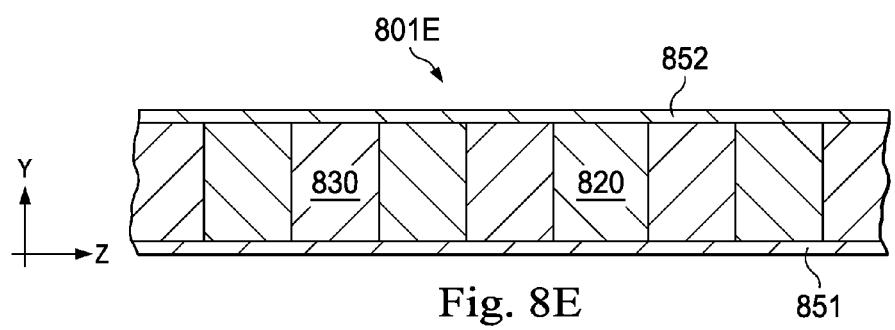

FIG. 8E illustrates the forming of a back electrode 851 in slab 801E. Back electrode 851 and front electrode 852 may be as electrodes 151 and 152 described in detail above (cf. FIG. 3). Back electrode 851 may be formed in the same way as front electrode 852 (cf. FIG. 8D). One of the advantages of SCC slab 801E is that it has relatively low acoustic impedance, so it can provide a broad frequency response even without an acoustic matching layer.

Figure 8F:
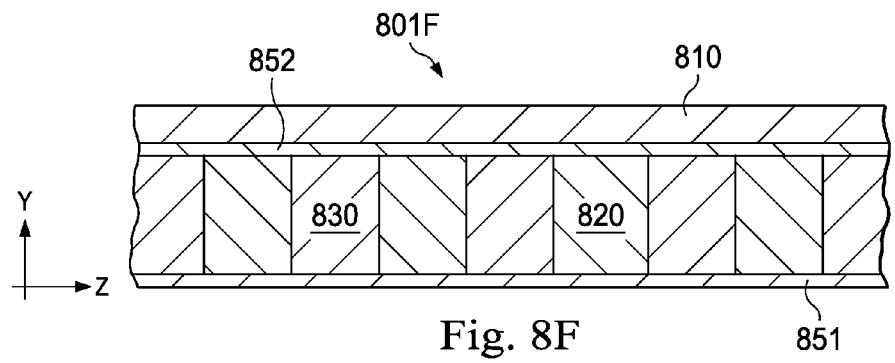

FIG. 8F illustrates slab SCC 801 formed by depositing an acoustic impedance matching layer 810 on top of slab 801E. Acoustic matching layer 810 is included in some embodiments of SCC 801 to match the acoustic impedance of the vessel tissue. Thus, acoustic matching layer 810 may further broaden the frequency response of an ultrasound transducer using SCC 801.

Once a slab of SCC 801 is complete as shown in FIG. 8E or FIG. 8F, it may be installed in a catheter tip as an ultrasound transducer. According to some embodiments, SCC 801 is pressed into molded tip 148 (cf. FIG. 4). Molded tip 148 may include a curved shape to impart a curved shape to SCC 801 and produce a focused acoustic beam 130. Molded tip 148 may also provide backing impedance to SCC 801 and attachment of the transducer to driveshaft 132 (cf. FIG. 4).

According to embodiments of the fabrication method illustrated in FIGS. 8A-F, the dimensions of an ultrasound transducer may be defined at the wafer level. Thus, the dimensions of a finished ultrasound transducer may be determined during the formation of slab 801A (e.g., photolithography step) and slab 801B (e.g., DRIE step). Furthermore, the finished ultrasound transducer may be segmented into smaller transducers of any desired size and shape. The flexibility of DRIE allows the formation of pillars 820 of arbitrary shape, forming arbitrary patterns within polymer matrix 830. For example, some pillar cross-sections discussed herein are more desirable than traditional square pillars. Having pillars 820 embedded in polymer matrix 830 allows the formation of a round transducer that is cut out using laser ablation.

By having flexibility in the layout and pattern design of an ultrasound transducer, fabrication methods for SCC layers as disclosed herein provide a focused ultrasound beam using a simple electrical coupling to the transducer. Some embodiments further include a custom electronic chip, such as a micro-electromechanical system (MEMS), to provide more sophisticated acoustic beam manipulation or modulation.

Figure 9:
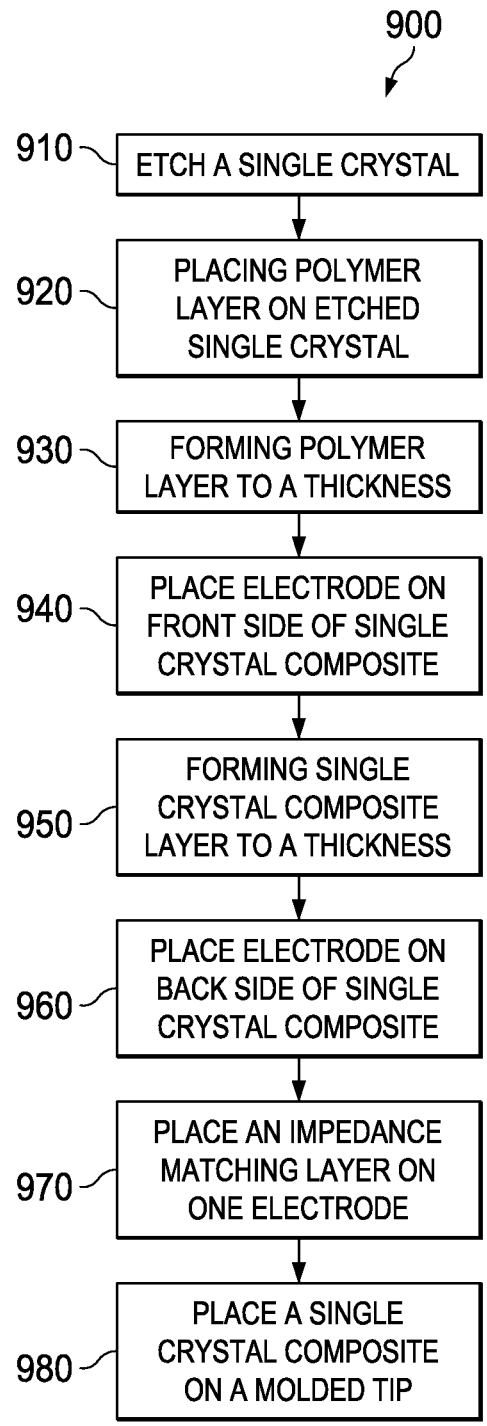
FIG. 9 shows a flow chart for a method of forming an ultrasound transducer according to some embodiments of the present disclosure.

FIG. 9 shows a flow chart for a method 900 of forming an ultrasound transducer according to embodiments disclosed herein. Method 900 will be described below in relation to the steps and structures illustrated in FIGS. 8A-F. Reference to the steps and structures in FIG. 8A-F is used for illustrative purposes only and is not limiting of the embodiments of method 900 consistent with the general concept expressed in FIG. 9. One of ordinary skill would recognize that obvious variations to method 900 may be provided, while maintaining the overall concept as described below.

Step 910 includes etching a single crystal according to a pattern formed by lithography, such as in slab 801A (cf. FIG. 8A). In some embodiments, step 910 includes a DRIE procedure. Step 920 includes placing a polymer layer on the etched single crystal, to form a slab such as slab 801B (cf. FIG. 8B). In some embodiments step 920 includes filling a pillar pattern resulting from the etching step 910 with polymer, which may be an epoxy. Step 930 includes forming the polymer layer to a thickness, such as in slab 801C (cf. FIG. 8C). Step 930 may include lapping the surface of the wafer to removing excess epoxy, creating a planar surface and exposing the pillars. In step 940 an electrode is placed on the front side of the SCC.

Step 950 includes forming an SCC layer to a thickness, as in slab 801D (cf. FIG. 8D). In some embodiments step 950 includes grinding the back portion of the wafer including slab 801D to release the composite structure from the wafer. Step 960 includes placing a back electrode to form a slab such as slab 801E (cf. FIG. 8E). According to some embodiments, step 960 may include similar procedures as step 940 to place front electrode 852 on slab 801D. In some embodiments, slab 801E is formed with a plurality of individual transducer elements, each forming an aperture. Step 960 may include cutting individual transducers from slab 801E. The cutting process could be made using a laser to cleanly remove epoxy filler 830 surrounding isolated groups of pillars 820. Thus, the piezoelectric material in pillars 820 may be left intact in step 960.

Step 970 includes placing an impedance matching layer on one electrode. Step 970 may include grinding the matching layer to a desired thickness.

Step 980 includes placing the SCC material thus formed on a molded tip, such as molded tip 148. Once the individual transducer is available, it can be pressed into a micro-molded housing that will become the tip of the flexible driveshaft in a rotational IVUS catheter. The molded housing may include a dish-shaped depression to form the desired aperture deflection. In some embodiments, step 980 is performed once the front and back electrodes are in place (steps 940 and 960). Step 980 may also include forming bonding pads to bridge the gap between the electrical leads inside the driveshaft (e.g., a shielded twisted pair) and the split back electrodes of the transducer. Such bonding pads may be as described in detail above in reference to bond pads 761-1 and 761-2 (cf. FIG. 7B). In some embodiments the fabrication process may include a "Cast-In-Can" method to form a transducer on a molded tip. In some embodiments, the transducer is pressed into the micro-molded tip subassembly. In some embodiments the transducer is placed on a molded tip such that acoustic beam 130 is formed in a plane perpendicular to the longitudinal axis of the catheter (XY plane in FIG. 2). According to some embodiments, the transducer is placed on a molded tip such that acoustic beam 130 extends at an oblique angle with respect to the longitudinal axis (Z-axis) of the catheter.

Embodiments of the present disclosure described above are exemplary only. One skilled in the art may recognize various alternative embodiments from those specifically disclosed. Those alternative embodiments are also intended to be within the scope of this disclosure. Accordingly, it is appropriate that the appended claims be construed broadly and in a manner consistent with the present disclosure.

What is claimed is:

1. A method of forming a single ultrasound transducer for use in IVUS imaging systems, the method comprising:
   etching a single crystal;
   placing a polymer layer on the etched single crystal to form a single crystal composite (SCC);
   forming the polymer layer to a first thickness;
   placing a first electrode on a first side of the SCC;
   forming the SCC to a second thickness;
   placing a second electrode on a second side of the SCC; and
   deforming the SCC to define a concave surface and an opposing convex surface, the deforming including forming an aperture having a diameter of an integer multiple of wavelengths of a center frequency of an ultrasound signal transmitted by the single transducer.

2. The method of claim 1 further comprising forming an index matching layer above the SCC layer, the index matching layer having a thickness of about ¼ wavelength of a center frequency of an ultrasound signal transmitted by the transducer.

3. The method of claim 1 wherein the deforming the SCC includes placing the SCC on a molded tip.

4. The method of claim 1 wherein deforming the SCC comprises forming a section of a sphere, the section having a depth of approximately 20 μm.

5. The method of claim 1 wherein the etching the single crystal comprises deep reactive ion etching.

6. The method of claim 1 wherein the etching the single crystal comprises defining a plurality of pillars.

7. The method of claim 6, wherein each of the pillars has a thickness-to-width aspect ratio of at least 2.

8. The method of claim 6, wherein each of the pillars has a cross section on a surface of the SCC with a shape selected from the group consisting of a circle, a square, a rectangle, and a figure from a random pattern.

9. The method of claim 1, wherein the placing the second electrode on the second side of the SCC includes placing two electrodes electrically decoupled from one another on the second side of the SCC.

10. The method of claim 1, wherein the convex surface of the SCC has a center of curvature along an axis of an ultrasound beam of the single ultrasound transducer.

11. A method of forming an intravascular ultrasound catheter, the method comprising:
    providing a single ultrasound transducer having:
      a single crystal composite (SCC) layer;
      a front electrode on a side of the SCC layer; and
      a back electrode on the opposite side of the SCC layer;
    wherein:
      the SCC layer includes pillars made of a single crystal piezoelectric material;
      the pillars are embedded in a polymer matrix; and
      the SCC layer has a concave upper surface and an opposing convex lower surface, and an aperture having a diameter of an integer multiple of wavelengths of a center frequency of an ultrasound signal transmitted by the single transducer; and
    coupling the single ultrasound transducer to a distal portion of an intravascular catheter.

12. The method of claim 11, wherein the coupling the single ultrasound transducer to the distal portion of the intravascular catheter includes coupling the single ultrasound transducer to a rotatable drive shaft.

13. The method of claim 11, wherein each of the pillars of the provided single ultrasound transducer has a thickness-to-width aspect ratio of at least 2.

14. The method of claim 11, wherein each of the pillars of the provided single ultrasound transducer has a cross section on a surface of the SCC with a shape selected from the group consisting of a circle, a square, a rectangle, and a figure from a random pattern.

15. The method of claim 11, wherein the back electrode of the provided single ultrasound transducer includes two electrodes electrically decoupled from one another.

16. The method of claim 11, wherein the convex surface of the SCC of the provided single ultrasound transducer has a center of curvature along an axis of an ultrasound beam of the single ultrasound transducer.

* * * * *